(12) United States Patent
Pathirana et al.

(10) Patent No.: US 7,893,016 B2
(45) Date of Patent: Feb. 22, 2011

(54) STABILISATION OF DOUBLE-STRANDED NUCLEIC ACIDS USING PROTEINS

(75) Inventors: Navin D. Pathirana, Cape Elizabeth, ME (US); Neil Butt, Cambridge (GB); Matthew Baker, Cambridge (GB)

(73) Assignee: GE Healthcare UK Ltd. (GB)

( * ) Notice: Subject to any disclaimer, the term of this patent is extended or adjusted under 35 U.S.C. 154(b) by 558 days.

(21) Appl. No.: 10/498,437

(22) PCT Filed: Dec. 11, 2002

(86) PCT No.: PCT/GB02/05617
§ 371 (c)(1),
(2), (4) Date: Apr. 29, 2005

(87) PCT Pub. No.: WO03/050278
PCT Pub. Date: Jun. 19, 2003

(65) Prior Publication Data
US 2005/0221307 A1  Oct. 6, 2005

(30) Foreign Application Priority Data
Dec. 11, 2001  (GB) ................................ 0129662.3

(51) Int. Cl.
*A61K 38/00* (2006.01)
*C12P 19/34* (2006.01)
(52) U.S. Cl. .................... 514/1.1; 530/300; 530/388.21
(58) Field of Classification Search ........................ None
See application file for complete search history.

(56) References Cited

U.S. PATENT DOCUMENTS 6,265,166 B1   7/2001   Frank-Kamenetskii et al.
7,244,561 B2 *  7/2007   Butt et al. ...................... 435/6

FOREIGN PATENT DOCUMENTS

| GB | 2 363 381 A   | 12/2001 |
|----|---------------|---------|
| WO | WO 00/21973   | 4/2000  |
| WO | WO 00/37686   | 6/2000  |
| WO | WO 01/96351 A1| 12/2001 |

OTHER PUBLICATIONS

Bertolaet, et al., 2001, Nature Structural Biology, 8, 417-422.*
Lund, et al., 1985, The Journal of Biological Chemistry, 260, 7609-7613.*
Su, et al., 2000, J. Mol. Biol., 303, 395-403.*
Guagliardi et al. (J. Mol. Biol., 267:841-848 (1997).*
Whitby, 1998, The Journal of Biological Chemistry, 273, 34983-34991.*
Jensen, 1980, Biochemica et Biophysica Acta, 624, 378-385.*
Ohmachi, 1989, Biochemistry, 28, 5226-5231.*
Votavova, 1986, Journal of Biomolecular Structure and Dynamics, 4, 477-489.*
Jansen, Lars E.T., "Preferential Binding of Yeast Rad4 Rad23 Complex to Damaged DNA," The Journal of Biological Chemistry, vol. 273, No. 50, pp. 33111-33114, XP-002239990, 1998.
Bertolaet, Bonnie L., "UBA Domains of DNA Damage-Inducible Proteins Interact with Ubiquitin," Nature Structural Biology, vol. 8, No. 5, pp. 417-422, XP-008016783, 2001.
Lafer, Eileen M., "The Effect of Anti-Z-DNA Antibodies on the B-DNA-Z-DNA Equilibrium," The Journal of Biological Chemistry, vol. 261, No. 14, pp. 6438-6443, XP-002248243, 1986.
Fermand, J.P., "Characterization of a Human Monoclonal IgM with Antibody Activity to dsDNA," Clin. Exp. Immunol., vol. 59, pp. 467-474, XP-008019805, 1985.
Müller, Hans-Peter, "Binding of Native $\alpha_2$ Macroglobulin to Human Group G Striptococci," Infection and Immunity, pp. 2833-2839, 1995.
Rantamäki, Liisa K., "Isolation and Characterization of $\alpha_2$ Macroglobulin from Mastitis Milk," Journal of Dairy Research, vol. 59, pp. 273-285; XP-008026036, 1992.
J. P. Fermand, et al., "Characterization of a Human Monoclonal IgM with Antibody Activity to dsDNA," Clin. Exp. Immunol. (1985) 59,467-474.
Annamaria Guagliardi, et al., "Annealing of Complementary DNA Strands Above the Melting Point of the Duplex Promoted by an Archaeal Protein," J. Mol. Biol. (1997) 267,841-848.
Andrew A. Travers, et al., "DNA Chaperones: A Solution to a Persistence Problem?", Cell, vol. 77, 167-169 (1994).
Patrick Sung, et al., "Renaturation of DNA Catalysed by Yeast DNA Repair and Recombination Protein RAD10," Nature, vol. 355, 743-745 (1992).
Junichi Kaburaki, et al., "Identification of Human Anti-DNA, Anti-RNP, Anti-SM, and Anti-SS-A Serum Antibodies Bearing the Cross-Reactive 16/6 Idiotype," The Journal of Immunology, vol. 139, 385-392, No. 2 (1987).
Apweiler, et al., "InterPro—an integrated documentation resource for protein families, domains and functional sites", Bioinformatics, vol. 16, No. 12, pp. 1145-1150, Dec. 2000.
Apweiler, et al., "The InterPro database, an integrated documentation resource for protein families, domains and functional sites", Nucleic Acids Research, 2001, vol. 29, No. 1, pp. 37-40.
Amstrong, et al., "$\alpha_2$-macroglobulin: an evolutionarily conserved arm of the innate immune system", Developmental and Comparative Immunology 23 (1999), pp. 375-390.
Baker, et al., "Isolation of Genomic DNA from Blood Using a Novel Filter-Based DNA Purification Technology", BioTechniques, vol. 31, No. 1, pp. 142-145, (2001).

(Continued)

Primary Examiner—Cecilia Tsang
Assistant Examiner—Satyanarayana R Gudibande
(74) Attorney, Agent, or Firm—Edwards Angell Palmer & Dodge LLP; David G. Conlin, Esq.; Kathryn A. Piffat, Esq.

(57) ABSTRACT

A composition for treating a nucleic acid duplex, wherein the composition is capable of inhibiting denaturation of the duplex, characterised in that the composition comprises a ubiquitin-like protein and/or a macroglobulin. It has been found that ubiquitin-like proteins (e.g. ubiquitin, NEDD8, RAD23, etc.) and macroglobulins (eg. $\alpha_2$-macroglobulin) are able to stabilise nucleic acid duplexes. A nucleic acid duplex which has been contacted with the composition of the invention can be subjected to more stringent processing conditions, with denaturation of the duplex being inhibited, than would otherwise be possible. Corresponding methods and uses are also provided.

11 Claims, 2 Drawing Sheets

OTHER PUBLICATIONS

Bucher, et al., "A Generalized Profile Syntax for Biomolecular Sequence Motifs and its Function in Automatic Sequence Interpretation", ISMB-94, Proceedings Second Internatonal Conference on Intelligent Systems for Molecular Biology, AAAI Press, Menlo Park, CA 94025, pp. 53-61, (1994).

Bukanov, et al., "PD-loop: A complex of duplex DNA with an oligonucleotide", Proc. Natl. Acad. Sci, USA, vol. 95, pp. 5516-5520, May 1998, Biochemistry.

Demidov, et al., Duplex DNA Capture, Curr. Issues Mol. Biol. vol. 2, No. 1, Jan. 2000, pp. 31-35.

Feige, et al., "$\alpha_2$-Macroglobulin: A Binding Protein for Transforming Growth Factor-$\beta$ and Various Cytokines", Horm Res 1996, 45, pp. 227-232.

Hofmann, et al., "The PROSITE database, its status in 1999", Nucleic Acids Research, 1999, vol. 27, No. 1, pp. 215-219.

LoConte, et al., "SCOP: a Structural Classification of Proteins database", Nucleic Acids Research, 2000, vol. 28, No. 1, pp. 257-259.

Silverstein, et al., The MetaFam Server: a comprehensive protein family resource, Nucleic Acids Research, 2001, vol. 29, No. 1, pp. 49-51.

Silverstein, et al., MetaFam: a unified classification of protein families. I. Overview and statistics, Bioinformatics, vol. 17, No. 3, 2001, pp. 249-261.

Shoop, et al., "MetaFam: a unified classification of protein families. II. Schema and query capabilities", Bioinformatics, vol. 17, No. 3, 2001, pp. 262-271.

Wong, et al., "General Method for HPLC Purification and Sequencing of Selected dsDNA Gene Fragments from Complex PCRs Generated during Gene Expression Profiling", BioTechniques, vol. 28, No. 4, pp. 776-783, Apr. 2000.

A. Guagliardi, et al., "Annealing of Complementary DNA Strands Above the Melting Point of the Duplex Promoted by an Archael Protein, " J. Mol. Biol. (1997) 267, pp. 841-848.

\* cited by examiner

FIGURE 2D

SEQUENCE LISTING

<160> NUMBER OF SEQ ID NOS: 1

<210> SEQ ID NO 1
<211> LENGTH: 26
<212> TYPE: PRT
<213> ORGANISM: Artificial Sequence
<220> FEATURE:

-continued

```
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: variable amino acid
<220> FEATURE:
<221> NAME/KEY: MOD_RES
<222> LOCATION: (3)
<223> OTHER INFORMATION: variable amino acid
<220> FEATURE:
<221> NAME/KEY: MOD_RES
<222> LOCATION: (4)
<223> OTHER INFORMATION: Leu, Ile, Val or Met
<220> FEATURE:
<221> NAME/KEY: MOD_RES
<222> LOCATION: (5)
<223> OTHER INFORMATION: variable amino acid
<220> FEATURE:
<221> NAME/KEY: MOD_RES
<222> LOCATION: (6)
<223> OTHER INFORMATION: Asp, Glu, Ser, Ala or Lys
<220> FEATURE:
<221> NAME/KEY: MOD_RES
<222> LOCATION: (7)
<223> OTHER INFORMATION: variable amino acid
<220> FEATURE:
<221> NAME/KEY: MOD_RES
<222> LOCATION: (8)
<223> OTHER INFORMATION: variable amino acid
<220> FEATURE:
<221> NAME/KEY: MOD_RES
<222> LOCATION: (9)
<223> OTHER INFORMATION: variable amino acid
<220> FEATURE:
<221> NAME/KEY: MOD_RES
<222> LOCATION: (10)
<223> OTHER INFORMATION: Leu, Ile, Val or Met
<220> FEATURE:
<221> NAME/KEY: MOD_RES
<222> LOCATION: (11)
<223> OTHER INFORMATION: Pro or Ala
<220> FEATURE:
<221> NAME/KEY: MOD_RES
<222> LOCATION: (12)
<223> OTHER INFORMATION: variable amino acid
<220> FEATURE:
<221> NAME/KEY: MOD_RES
<222> LOCATION: (13)
<223> OTHER INFORMATION: variable amino acid
<220> FEATURE:
<221> NAME/KEY: MOD_RES
<222> LOCATION: (14)
<223> OTHER INFORMATION: variable amino acid
<220> FEATURE:
<221> NAME/KEY: MOD_RES
<222> LOCATION: (16)
<223> OTHER INFORMATION: variable amino acid
<220> FEATURE:
<221> NAME/KEY: MOD_RES
<222> LOCATION: (17)
<223> OTHER INFORMATION: Leu, Ile, Val or Met
<220> FEATURE:
<221> NAME/KEY: MOD_RES
<222> LOCATION: (18)
<223> OTHER INFORMATION: Leu, Ile, Val, Met or Cys
<220> FEATURE:
<221> NAME/KEY: MOD_RES
<222> LOCATION: (19)
<223> OTHER INFORMATION: Leu, Ile, Val, Met, Phe or Tyr
<220> FEATURE:
<221> NAME/KEY: MOD_RES
<222> LOCATION: (20)
<223> OTHER INFORMATION: variable amino acid
<220> FEATURE:
<221> NAME/KEY: MOD_RES
<222> LOCATION: (22)
<223> OTHER INFORMATION: variable amino acid
<220> FEATURE:
```

```
-continued
<221> NAME/KEY: MOD_RES
<222> LOCATION: (23)
<223> OTHER INFORMATION: variable amino acid
<220> FEATURE:
<221> NAME/KEY: MOD_RES
<222> LOCATION: (24)
<223> OTHER INFORMATION: variable amino acid
<220> FEATURE:
<221> NAME/KEY: MOD_RES
<222> LOCATION: (25)
<223> OTHER INFORMATION: variable amino acid
<220> FEATURE:
<221> NAME/KEY: MOD_RES
<222> LOCATION: (26)
<223> OTHER INFORMATION: Asp or Glu

<400> SEQUENCE: 1

Lys Xaa Xaa Xaa Xaa Xaa Xaa Xaa Xaa Xaa Xaa Xaa Xaa Xaa Gln Xaa
 1               5                  10                  15

Xaa Xaa Xaa Xaa Gly Xaa Xaa Xaa Xaa Xaa
            20                  25
```

STABILISATION OF DOUBLE-STRANDED NUCLEIC ACIDS USING PROTEINS

All documents cited herein are incorporated by reference in their entirety.

CROSS-REFERENCES TO RELATED APPLICATIONS

The present application is a 35 U.S.C. §371 national stage of PCT application PCT/GB002/05617, filed Dec. 11, 2002, which claims priority of United Kingdom Application Serial Number 0129662.3, filed Dec. 11, 2001, the disclosures of all of which are incorporated herein by reference.

TECHNICAL FIELD

This invention is in the field of nucleic acid preparation and relates to reagents and methods for stabilising nucleic acid duplexes.

BACKGROUND ART

Many purification techniques include a heating step. It is difficult to purify double-stranded DNA using these techniques because heating causes denaturation of double stranded DNA (dsDNA) duplexes to form single-stranded DNA (ssDNA). This causes problems for any downstream DNA processing techniques which require dsDNA.

Various methods for stabilising double-stranded nucleic acids are known. For examples, reference 1 reviews the sequence-specific isolation and purification of intact dsDNA by oligonucleotide/PNA -assisted affinity capture. References 2 & 3 discuss the use of the PD-loop in the isolation of dsDNA fragments from complex mixtures. Reference 4 discloses the use of ion-pair reversed-phase HPLC to purify dsDNA. Other methods are discussed in the introduction to references 5 and 6, and commercially-available kits include the Wizard™ Genomic DNA Purification Kit (Promega), FlexiPrep™ (Pharmacia Biotech) and Whatman Bio-Science's Genomic DNA Purification System ('WBPS'; ref. 7).

Reference 5 discloses methods and reagents for stabilising dsDNA. It discloses an aqueous solution for treating a nucleic acid duplex having a pH of from 3 to 11 and comprising (a) a soluble protein or mixture of proteins and (b) 0.1 mM to 10 mM divalent cations. The nature and concentration of the soluble protein or mixture of proteins is selected so that the solution is capable of inhibiting heat denaturation of a nucleic acid duplex.

The preferred proteins used in reference 5 are from mammalian blood serum. By its nature, however, serum is a complex mixture. It would be advantageous to achieve the same effects as disclosed in reference 5 using simpler and/or more defined reagents. It is therefore an object of the invention to provide improved reagents, methods and compositions for use in stabilising nucleic acid duplexes such as dsDNA.

DISCLOSURE OF THE INVENTION

It has surprisingly been found that ubiquitin-like proteins and macroglobulins can stabilise nucleic acid duplexes.

The invention provides a composition for inhibiting denaturation of a nucleic acid duplex, characterised in that the composition comprises a ubiquitin-like protein. The invention also provides a composition for inhibiting denaturation of a nucleic acid duplex, characterised in that the composition comprises a macroglobulin. The invention also provides a composition for inhibiting denaturation of a nucleic acid duplex, characterised in that the composition comprises a ubiquitin-like protein and a macroglobulin.

A nucleic acid duplex which has been contacted with the composition of the invention can be subjected to more stringent processing conditions than would otherwise be possible, with denaturation of the duplex being inhibited. The invention assists in purifying double-stranded nucleic acids from complex mixtures and allows, for instance, dsDNA to be preserved in its intact biologically active form (e.g. for studying epigenetic modifications in imprinted genes).

The invention also provides a method for inhibiting the denaturation of a nucleic acid duplex, comprising the step of contacting a nucleic acid duplex with a composition of the invention.

The invention also provides the use of the composition of the invention for inhibiting denaturation of a nucleic acid duplex.

The invention also provides a method for purifying a nucleic acid duplex, comprising the step of contacting the nucleic acid duplex with a composition of the invention. The invention also provides a method for purifying a nucleic acid duplex from a sample, comprising the step of contacting the sample with a composition of the invention.

The invention also provides a method in which two nucleic acids (e.g. single stranded) are contacted under hybridising conditions to form a nucleic acid duplex, wherein the method comprises the subsequent step of contacting the duplex with a composition of the invention.

The invention also provides a process for extracting or purifying double-stranded nucleic acid from a biological sample which includes cells, comprising the steps of: (a) lysing cells which contain nucleic acid, to form a cell lysate; (b) contacting the cell lysate with a composition of the invention; and (c) purifying nucleic acid from the lysate, optionally including heating the lysate. The lysis step may take place on a filter, which conveniently allows treatment of the sample and the lysate (e.g. retention of cells in a sample, washing steps etc.) on a single support. Preferably the filter composition and dimensions are selected so that the nucleic acid is retained by the filter substantially in the absence of ionic interaction [e.g. ref. 8]. If a cell lysate is already available, step (a) is optional.

The invention provides a composition comprising: (1) a cell lysate; and (2) a ubiquitin-like protein and/or a macroglobulin.

The invention also provides a kit for isolating nucleic acid from a sample comprising cells containing nucleic acid, comprising a composition of the invention and a filter.

The invention provides a complex of a nucleic acid duplex and a ubiquitin-like protein. The invention also provides a complex of a nucleic acid duplex and a macroglobulin. These complexes are preferably in substantially pure form (e.g. free from cellular debris).

The invention also provides a product for use in affinity capture of double-stranded nucleic acid, comprising a ubiquitin-like protein and/or a macroglobulin immobilised on a solid support.

The Nucleic Acid Duplex

The invention can be used with any appropriate nucleic acid duplex, but will typically be used with DNA/DNA duplexes (i.e. with dsDNA).

Other suitable duplexes may be formed from single-stranded molecules including both RNA and DNA. This includes analogues, such as those containing modified backbones (e.g. phosphorothioates) and peptide nucleic acids (PNA), as well as hybrid molecules (e.g. DNA-RNA hybrids). Duplexes for use according to the invention therefore include, without limitation: RNA/RNA duplexes; DNA/RNA duplexes; DNA/PNA duplexes, PNA/PNA duplexes, PNA/RNA duplexes etc.

The duplex nucleic acid may be in any form e.g. A, B, C, Z etc.

Inhibition of denaturation can readily tested by the skilled person by a comparison of the behaviour of a duplex contacted with (a) the composition of the invention or (b) a standard wash solution (e.g. water, or a low-salt nucleic acid preserving solution such as AE or the like). A convenient way of comparing denaturation is to compare the melting temperature ($T_m$) of the duplex in (a) and (b) e.g. using a parameter such as $OD_2 60$ (i.e. measuring the hyperchromic effect) or density. Denaturation can also be compared in (a) and (b) by using reagents specific for double- or single-stranded nucleic acids e.g. the amount of dsDNA in (a) and (b) can be compared using anti-dsDNA antibodies. Other methods which can be used include spectroscopic methods, and the differential affinity of dsDNA and ssDNA for hydroxyapatite [see also ref. 9].

Denaturation of the duplex is inhibited using the composition of the invention. The extent of inhibition may range from a relatively small degree to substantially complete inhibition depending on various factors (e.g. pH, ionic strength, the nature and concentration of cations, temperature, duration of beating etc.) but inhibition is preferably at least 50% (e.g. 60%, 70%, 80%, 90%, 95%, 98%, 99%, or even 100%) compared to a control in which the composition of the invention is not used.

Denaturation may be caused by, for example, temperature, salt concentration, pH etc.

Preferred compositions inhibit denaturation so that in excess of 50% of a nucleic acid duplex sample is maintained in duplex form when the sample is subjected to a temperature of 90° C. for up to 30 minutes, more preferably 100° C. for up to 1 hour.

In some embodiments of the invention, the components of the composition are selected so as to inhibit denaturation of some duplexes whilst allowing other (weaker) duplexes to be denatured. In other words, the denaturation of inhibition is at least partially specific.

Although it is preferred that the composition of the invention is contacted with a nucleic acid duplex prior to subjecting the duplex to denaturing conditions, it is also possible for the nucleic acid duplex to be subjected to mild denaturing conditions (e.g. a degree of heating) followed by contacting the duplex with the composition of the invention, with the duplex then being subjected to harsher denaturing conditions.

Characteristics of the Composition

The composition of the invention will typically be in the form of an aqueous solution. DNA undergoes depurination and structural degradation below pH 3, and denaturation is favoured above pH 11. The pH of the composition of the invention is therefore generally between 3 and 11, preferably between 4 and 10, more preferably between 5 and 9, and most preferably between 6 and 8. A typical pH will be neutral i.e. around pH 7.0, although the optimum pH for dsDNA-binding will be different for each particular ubiquitin-like protein or macroglobulin.

The pH of the composition is preferably controlled using a buffer e.g. Tris, phosphate buffer, histidine buffer, PIPES, HEPES etc. In addition, the composition is preferably sterile.

The composition will generally comprise divalent cations. These will generally be present at a concentration between 0.1 mM and 10 mM, preferably between 0.5 mM and 8 mM, more preferably between 1 mM and 5 mM, and most preferably between 2 and 4 mM. A typical concentration of divalent cations will be around 3 mM, although the optimum concentration for dsDNA-binding will be different for each particular ubiquitin-like protein or macroglobulin.

Preferred divalent cations are $Mg^{2+}$ ions.

It is preferred, but not essential, that a solution of the invention additionally comprises monovalent cations. These will generally be present at a concentration between 0.1 mM and 100 mM, preferably between 1 mM and 50 mM, more preferably between 5 mM and 15 mM, and most preferably between 7 and 10 mM. A typical concentration of monovalent cations will be around 8 mM, although the optimum pH for dsDNA-binding will be different for each particular ubiquitin-like protein or macroglobulin.

Preferred monovalent cations are $K^+$ or $Na^+$ ions.

The components of the composition of the invention can be mixed in any convenient order. In general, however, proteins are added at the end of mixing to avoid precipitation, and any monovalent cations are preferably added after divalent cations.

The composition may contain a low concentration of an antimicrobial agent (e.g. $Na_2S_2O_5$).

The composition is preferably free from serum (e.g. free from FCS).

The composition of the invention may take the form of a drycomposition which can be dissolved in an aqueous medium. In these circumstances, it will be appreciated that the above characteristics of the composition relate to the resulting aqueous composition.

The ubiquitin-like protein and macroglobulin in the composition can take various forms e.g. a fusion protein, a tandem repeat protein, a precursor, a mature protein, glycosylated, unglycosylated, methylated, labelled (e.g. biotinylated), with or without N-terminal methionine etc. provided that duplex-stabilisation activity is retained.

The ubiquitin-like protein and/or macroglobulin will typically be present at a concentration of between 0.1 and 20 mg/ml, preferably between 0.25 and 10 mg/ml, more preferably between 0.5 and 5 mg/ml, and most preferably between 1 and 3 mg/ml.

The Ubiquitin-Like Protein

Ubiquitin is a highly-conserved 76 amino acid protein found in all eukaryotic cells and whose sequence is extremely well conserved from protozoa to vertebrates. In most species, there are many genes coding for ubiquitin. These fall into two classes. The first class produces polyubiquitin molecules consisting of exact head to tail repeats of ubiquitin. The number of repeats is variable. In the majority of polyubiquitin precursors, there is a final amino-acid after the last repeat. The second class of genes produces precursor proteins consisting of a single copy of ubiquitin fused to a Cterminal extension protein (CEP). There are generally two types of CEP proteins, both being ribosomal proteins. Any ubiquitin from any suitable species can be used according to the invention, as can any of the large number of proteins which are evolutionary related to ubiquitin. DNA-binding activity for these proteins has not previously been reported.

The compositions of the invention comprise a ubiquitin-like protein. This protein may be any of the following: (a) a protein which satisfies the ubiquitin domain signature of PROSITE (entry PS00299); (b) a protein which satisfies the ubiquitin domain profile of PROSITE (entry PS50053; Table 1 herein); (c) a protein which satisfies the requirements of superset 368 of METAFAM; (d) a protein which satisfies the requirements of InterPro entry IPR000626; or (e) a protein in the 'Ubiquitin-like' superfamily of the Structural Classification of Proteins database (SCOP); Proteins in categories (a) and (b) are preferred (see PROSITE documentation entry PDOC00271).

The PROSITE database is described in further detail in reference 10, and more details about PROSITE profiles can be found in reference 11. The METAFAM database is described in further detail in references 12, 13 and 14. The InterPro database is described in further detail in references 15 and 16. The SCOP database is described in further detail in reference 17. Determining whether a protein satisfies a particular PROSITE, METAFAM, SCOP or InterPro database entry is routine using widely available software tools.

For group (a), the ubiquitin domain signature consensus pattern in release 16.51 of PROSITE is (SEQ ID NO: 1)

K-x(2)-[LIVM]-x-[DESAK]-x(3)-[LIVM]-[PA]-x(3)-Q-x-[LIVM]-[LIVMC]-[LIVMFY]-x-G-x (4)-[DE]

Any protein containing an amino acid sequence which satisfies this consensus pattern can be used according to the invention (see also Table 2 herein).

For group (b), the ubiquitin domain profile in release 16.51 of PROSITE is shown in Table 1. Any protein containing an amino acid sequence which satisfies this profile can be used according to the invention.

Within group (e), the five families in release 1.55 of SCOP are: (1) Ubiquitin -related; (2) UBX domain; (3) Golgi-associated ATPase enhancer of 16 kD, Gate-16; (4) First domain of FERM; and (5) Ras-binding domain, RBD. Proteins from any of these five families can be used, but it is preferred to use a protein from the 'ubiquitin-related' family. The five SCOP domains within the 'ubiquitin-related' family are: (1) ubiquitin; (2) SUMO-1 (smt3 homologue); (3) Nedd8; (4) Elongin B; and (5) Rubl. Any protein within these five families can be used with the invention.

Specific examples of ubiquitin-like proteins which can be used according to the invention are: ubiquitin; mammalian protein GDX (preferably the N-terminal 74 residues); mammalian protein FAU (preferably the N-terminal 74 residues); mouse protein NEDD8; human protein BAT3 (preferably the N-terminal domain); *Caenorhabditis elegans* protein ubl-1 (preferably the N-terminal 70 residues); yeast DNA repair protein RAD23 (preferably the N-terminal domain); mammalian RAD23-related proteins RAD23A and RAD23B; mammalian BCL-2 binding athanogene-1 (BAG-1) (preferably the central domain); human spliceosome associated protein 114 (SAP 114 or SF3A120); yeast protein DSK2 (preferably the N-terminal domain); human protein CKAP1/TFCB; *Schizosaccharomyces pombe* protein alp II; *Caenorhabditis elegans* hypothetical protein F53F4.3; *Schizosaccharomyces pombe* hypothetical protein SpAC26A3.16; yeast protein SMT3; human ubiquitin-like proteins SMT3A and SMT3B; human ubiquitin-like protein SMT3C (also known as PIC1; Ubl1, Sumo-1; Gmp-1 or Sentrin); SMT3-like proteins in plants and *Caenorhabditis elegans*; ISG15 (also known as UCRP); *S. cerevisiae* protease Ubp6. The invention can utilise these proteins from any organism.

Preferred ubiquitin-like proteins for use with the invention are NEDD8, ubiquitin and RAD23. Other preferred ubiquitin-like proteins are those with a positive surface charge.

Sequences for all of these proteins are readily available from public databases (e.g. from GenBank; see also field DR in Table 1), as are sequence alignments (see PFAM, METAFAM etc.). It will be appreciated that the protein which is used according to the invention may comprise one of these sequences or may alternatively have: (a) an amino sequence which has greater than x % sequence identity thereto; and/or (b) an amino acid sequence comprising at least n consecutive amino acids therefrom. The value of x is 50 or more (e.g. 60, 70, 80, 90, 95, 99 or more). The value of n is 7 or more (e.g. 8, 10, 12, 14, 16, 18, 20, 30, 40, 50, 60, 70, 80, 90, 100, 150, 200 or more). These sequences (a) and (b) include homologs, orthologs, allelic variants and functional mutants (e.g. a Gly76→Ala mutant of NEDD8 is commercially available). Sequence identity is preferably determined by the Smith Waterman homology search algorithm as implemented in the MPSRCH program (Oxford Molecular), using an affine gap search with parameters gap open penalty=12 and gap extension penalty=1.

In a composition of the invention, the ubiquitin-like protein will typically comprise at least 10% by weight of the total protein in the composition (e.g. 20%, 30%, 40%, 50%, 60%, 70%, 80%, 90%, 95%, 98%, 99% or more). If the ubiquitin-like protein is a fusion protein, the fusion partner is included within this figure (i.e. the fusion protein comprises at least 10% by weight of the total protein in the composition).

The ubiquitin-like protein is preferably in oligomeric form (e.g. a dimer, trimer, tetramer etc.).

The compositions of the invention may comprise mixtures of one or more ubiquitin-like proteins.

Without wishing to be bound by theory, it is thought that the ubiquitin-like protein in the composition of the invention causes a stability change in nucleic acid duplexes. It is thought that the stability change may involve the protein wrapping-around the duplex as a result of specific or non-specific binding to the protein.

The Macroglobulin

Macroglobulins are high MW antibodies that accumulate in the blood. The macroglobulin for use according to the invention is preferably an α-macroglobulin, and more preferably an $\alpha_2$-macroglobulin. The α-macroglobulins are protease inhibitors which have been isolated in many organisms (e.g. mammals and arthropods). Their inhibitory activity does not result from competitive inhibition of proteases, but from an ability to form "cages" around protease enzymes which block access of high MW substrates to the active site.

As well as having protease inhibitory activity, the $\alpha_2$-macroglobulins are able to bind and neutralize some growth factors, including TGF-β. In macrophages, $\alpha_2$-macroglobulins induce synthesis of nitric oxide synthase; in vascular smooth muscle cells, $\alpha_2$-macroglobulins induce expression of platelet-derived growth factor α receptor. Further details are given in refs. 18 & 19.

For use with the invention, the macroglobulin should retain its protease inhibitory activity, as denatured $\alpha_2$-macroglobulin which could not inhibit trypsin was found not to stabilise dsDNA.

The macroglobulin is preferably in oligomeric form (e.g. a dinner, trimer, tetramer etc.).

The compositions of the invention may comprise mixtures of one or more macroglobulins.

Integration into Techniques for Dealing with Nucleic Acids

The stabilisation of duplexes by use of the invention can be integrated into any appropriate technique which uses double-stranded nucleic acids. The invention is particularly suited to stabilising genomic dsDNA e.g. during its purification. For example, a stabilised duplex may be subjected to downstream processing e.g. one or more steps of purification, analysis, ligation, enzymatic treatment (e.g. restriction enzyme digestion), amplification (e.g. PCR), denaturation, hybridisation, expression, sequencing, separation, etc.

The duplex to be stabilised may be the product of a hybridisation-based technique in which a labelled probe is hybridised to a nucleic acid sample. Such techniques include blotting (Southern, Northern, slot, dot etc.), microarray hybridisation, in situ hybridisation (e.g. FISH) etc. The invention allows hybridisation products to be protected against denaturation during downstream processing steps in the technique i.e. it allows the duplex to be subjected to more stringent downstream conditions than would otherwise be possible. For example, the nucleic acid duplex may be subjected to more stringent wash conditions (e.g. washing at an elevated temperature).

The invention allows dsDNA to be purified directly from an amplification reaction or from an agarose gel slice. Amplification products can be separated from contaminants such as primers.

The composition of the invention may be used in methods known under the trade names FTA/FTA elute™, Genspin™ and Genprep™.

The invention is particularly suited for use with methods for extracting or purifying dsDNA (e.g. genomic DNA) from samples which include cells (e.g. from blood samples). The invention provides a process for purifying double-stranded nucleic acid [cf. ref. 8] comprising the steps of:
(a) applying a sample comprising cells which contain nucleic acid to a filter, whereby the cells are retained as a retentate and contaminants are removed;
(b) lysing the retentate from step (a) whilst the retentate is retained by the filter to form a cell lysate containing the nucleic acid;
(c) filtering the cell lysate with the filter to retain the nucleic acid and remove remaining cell lysate;
(d) optionally washing the nucleic acid retained by the filter; and
(e) eluting the nucleic acid, wherein at least one step of the process is performed in the presence of a ubiquitin-like protein and/or a macroglobulin.

The filter used in step (c) preferably retains nucleic acid substantially in the absence of ionic interactions.

Steps (a) to (e) are preferably performed between 0° C. and 100° C. The process will generally be performed at between 20 and 50° C. (e.g. between 25 and 40° C., or around 35° C.), although individual steps in the overall process may involve heating or cooling outside this range.

Extraction of double-stranded nucleic acid by the methods of the invention enables a required sample to be obtained in a significantly shorter period of time as compared with previous extraction methods.

BRIEF DESCRIPTION OF DRAWINGS

FIG. 2 shows models of charge fields surrounding various ubiquitin domain structures. Blue shows positive charge; red shows negative charge. DNA is shown in yellow and grey. The proteins shown are: (2A) ubiquitin; (2B) RAD23A; (2C) SUMO-1; (2D) NEDD8.

MODES FOR CARRYING OUT THE INVENTION

References 5 and 6 disclose that FCS can stabilise nucleic acid duplexes. The activity of FCS was compared to ubiquitin.

The comparison was carried out using 1 ml WBPS columns according to the standard protocol [7]. Briefly, 0.5 ml blood was added to columns with 0.0.5 ml 'solution 1' (a red blood cell lysis solution) and the column is eluted by vacuum pump. A further 1 ml of 'solution 1' was then added, followed by vacuum elution. At this stage, white blood cells are captured within the filter and red blood cells have been removed. 1 ml of 'solution 2' (a white blood cell lysis solution) was then added to lyse the trapped cells, followed by vacuum elution. The filter was then washed with 1 ml of either 'solution 3' (1% FCS; KCl, MgCl$_2$, Tris; pH ~7) or 'solution 3' in which FCS was replaced by ubiquitin (Sigma, product code U6253) from bovine erythrocytes. After vacuum elution, 100 µl TE was added and the column was heated to 80° C. for 10 minutes. After heating, 200 µl TE was added. Elution gives dsDNA from the blood sample.

Various concentrations of ubiquitin were tested, and results were as follows:

| Ubiquitin concentration (mg/ml) | Concentration of dsDNA (ng/µl) ± SD | dsDNA yield (µg/ml blood) ± SD |
| --- | --- | --- |
| 0.00 | 2.85 ± 0.26 | 0.84 ± 0.08 |
| 0.10 | 3.11 ± 0.29 | 0.85 ± 0.10 |
| 0.25 | 4.52 ± 0.50 | 1.25 ± 0.18 |
| 0.50 | 12.70 ± 10.14 | 3.65 ± 3.14 |
| 1.00 | 13.59 ± 1.32 | 3.89 ± 0.51 |
| 2.00 | 22.37 ± 1.76 | 6.47 ± 0.63 |
| 2.50 | 20.96 ± 6.04 | 6.21 ± 1.70 |

For comparison, the concentration of dsDNA obtained under the same conditions using FCS-containing 'solution 3' was 17.86±3.41 ng/µl (i.e. yield of 5.37±1.25 µg/ml blood). The stabilising effect of 1% FCS can therefore be achieved using between 1 and 2 mg/ml ubiquitin.

Similar experiments were performed on blood using higher ubiquitin concentrations:

| Ubiquitin concentration (mg/ml) | Concentration of dsDNA (ng/µl) ± SD |
| --- | --- |
| 0.0 | 2.25 ± 0.58 |
| 2.5 | 27.06 ± 5.91 |
| 5.0 | 30.87 ± 4.93 |

For comparison, the concentration of dsDNA obtained under the same conditions using WBPS 'solution 3' was 15.49±10.49 ng/µl.

NEDD8 is related to ubiquitin and the dsDNA-stabilising activity of NEDD8 was also tested. Solutions were prepared in the same way as the ubiquitin solutions (i.e. WBPS 'solution 3' but with NEDD8 instead of FCS; pH 7-8). Two forms of NEDD8 were used (a native sequence and a 'control' form with a Gly76→Ala mutation, which cannot conjugate), both as GST-fusion proteins. SUMO-1 and $α_2$-macroglobulin were also tested. All proteins were compared to the results obtained using WBPS 'solution 3' (and, as a negative control, against 'solution 3' lacking its FCS component).

These assays were performed using WBPS reagents, but in a 96-well format which uses a slightly modified protocol. Briefly, 0.4 ml blood was mixed with 0.4 ml 'solution 1'. After vacuum, a further 0.8 ml of 'solution 1' was then added (vacuum), followed by 0.3 ml 'solution 2' (incubation period 5 minutes, then vacuum). The wells were then incubated for 5 minutes with 0.3 ml of either 'solution 3' or an equivalent solution in which FCS was replaced by the protein under investigation. After vacuum, 25 µl TE was added and the column was heated to 50° C. for 10 minutes. After heating, 200 µl TE was added and the TE was sucked out and collected. The eluted TE contains dsDNA from the blood sample.

Results were as follows:

| Composition | Concentration | dsDNA concentration (ng/μl) |
|---|---|---|
| Ubiquitin | 1.16 mg/ml | 22.34 ± 9.99 |
| Ubiquitin | 0.49 mg/ml | 13.07 ± 7.37 |
| NEDD8 | 0.49 mg/ml | 68.64 ± 16.63 |
| NEDD8 (G76A) | 0.49 mg/ml | 50.33 ± 8.22 |
| SUMO-1 (G76A) | 1 mg/ml | 2.60 ± 0.35 |
| $\alpha_2$-macroglobulin | 5 mg/ml | 10.79 ± 0.54 |
| 'Solution 3' (1% FCS) | 1% FCS | 26.35 ± 7.26 |
| 'Solution 3' (0% FCS) | Control | 1.35 ± 0.13 |

The data in this table show that both forms of NEDD8 are more active than ubiquitin in stabilising dsDNA, and that the stabilising activity is independent of NEDD8's ability to conjugate to target proteins.

NEDD8 was used in the form of GST-fusion proteins, in which NEDD8 makes up only 24% by weight. Ubiquitin and NEDD8 both have MW ~8 kDa so, at the same concentration (0.49 mg/ml), NEDD8-GST represents about 4× less active protein than ubiquitin. Taking this into account, the specific activity of NEDD8 is around 20 times greater than that of ubiquitin.

Figure 1:
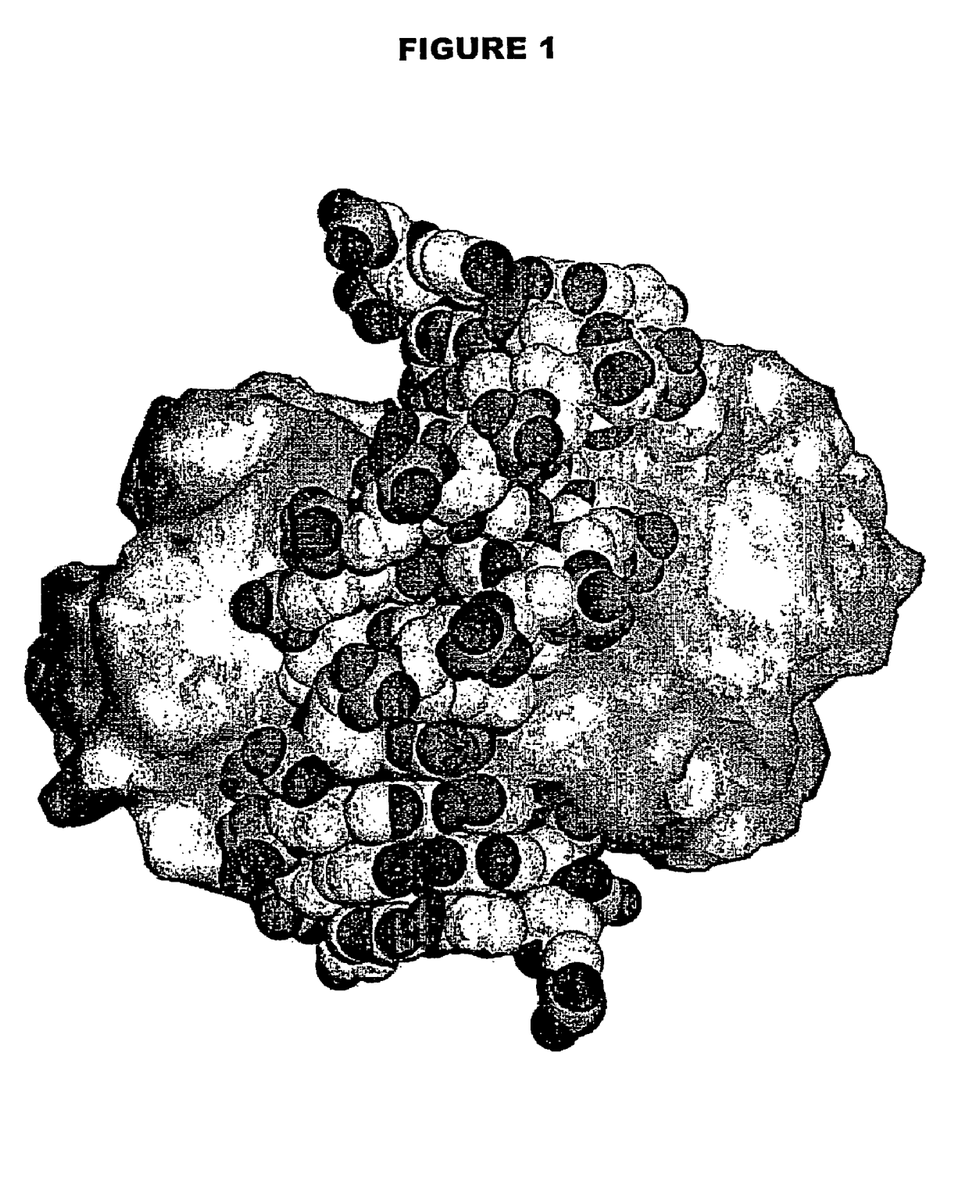
FIG. 1 shows a molecular model of interactions between a DNA duplex and a ubiquitin dimer.
Figure 2A:
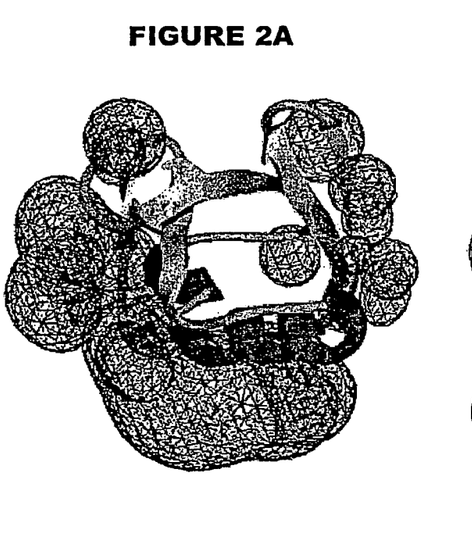
Figure 2B:
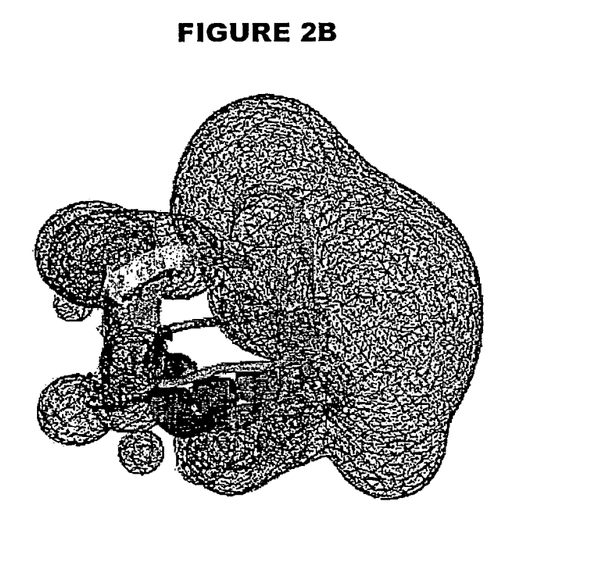
Figure 2C:
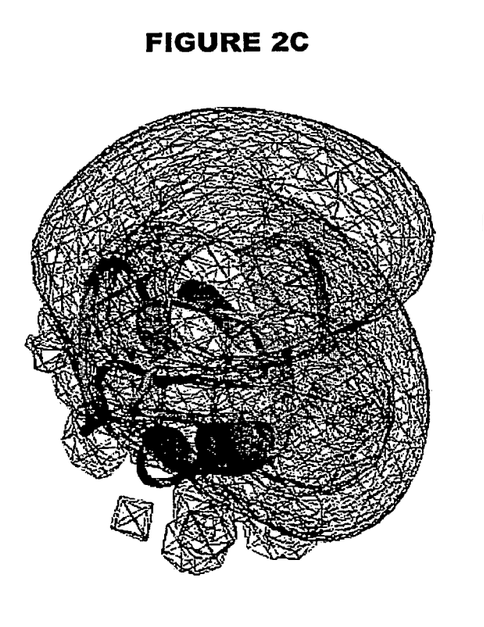
Figure 2D:
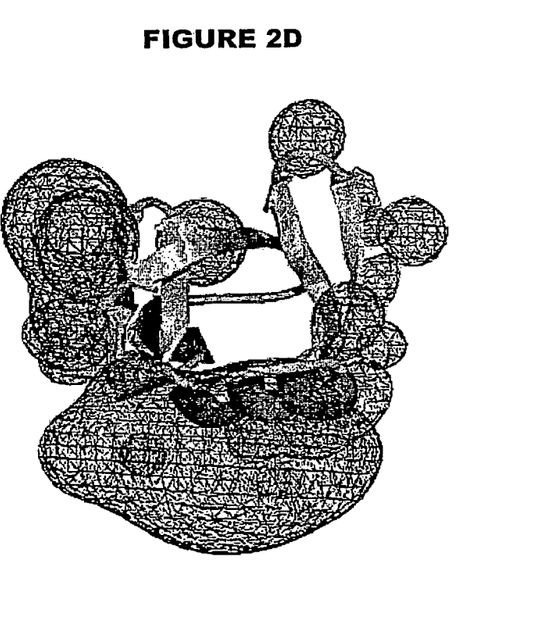

Computer modelling (using Deep View 37b2 and ProModII v.3.5) suggests that a dimer of ubiquitin can form a groove which can accommodate dsDNA (FIGS. 1 & 2A). The charge field surrounding the dimer in this model is fairly positive, enabling the negative DNA backbone to be held in place. A similar field is seen in NEDD8 (FIG. 2D) and also in RAD23 (FIG. 2B). The charge surrounding SUMO1, however, is different (FIG. 2C). The experimental data obtained using SUMO1 support the view that the charge field of a ubiquitin-like protein is important in determining dsDNA stabilising activity.

The results obtained with $\alpha_2$-macroglobulin were investigated further. Two forms of $\alpha_2$-macroglobulin were tested—a form which did not inhibit trypsin (Sigma code M7151) and a form which did inhibit trypsin (Sigma code M6159). The M6159 preparation was able to stabilise dsDNA whereas the M7151 form was not:

| Composition | Concentration | dsDNA concentration (ng/μl) |
|---|---|---|
| $\alpha_2$-macroglobulin (M6159) | 5 mg/ml | 10.79 ± 0.54 |
| $\alpha_2$-macroglobulin (M7151) | 0.1 mg/ml | 2.36 ± 0.25 |
| $\alpha_2$-macroglobulin (M7151) | 0.5 mg/ml | 1.86 ± 0.13 |
| $\alpha_2$-macroglobulin (M7151) | 2.5 mg/ml | 1.43 ± 0.19 |
| $\alpha_2$-macroglobulin (M7151) | 5.0 mg/ml | 1.16 ± 0.07 |
| WBPS (0% FCS) | Control | 2.25 ± 0.58 |

The data in this table show that $\alpha_2$-macroglobulin which is unable to inhibit trypsin activity (i.e. which is somehow denatured) is unable to stabilise dsDNA, whereas $\alpha_2$-macroglobulin which can inhibit trypsin activity (i.e. which is not denatured) can stabilise dsDNA.

It will be understood that the invention has been described by way of example only and modifications may be made whilst remaining within the scope and spirit of the invention.

TABLE 1

PROSITE PROFILE PS50053

ID UBIQUITIN_2; MATRIX.
AC PS50053;
DT NOV-1997 (CREATED); NOV-1997 (DATA UPDATE); JUL-1998 (INFO UPDATE).
DE Ubiquitin domain profile.
MA /GENERAL_SPEC: ALPHABET='ABCDEFGHIKLMNPQRSTVWYZ'; LENGTH=76;
MA /DISJOINT: DEFINITION=PROTECT; N1=6; N2=71;
MA /NORMALIZATION: MODE=1; FUNCTION=LINEAR; R1=.1843; R2=.02177539; TEXT='NScore';
MA /CUT_OFF: LEVEL=0; SCORE=381; N_SCORE=8.5; MODE=1;
MA /CUT_OFF: LEVEL=-1; SCORE=290; N_SCORE=6.5; MODE=1;
MA /DEFAULT: D=-20; I=-20; B1=-30; E1=-30; MI=-105; MD=-105; IM=-105; DM=-105; MM=1; M0=-1;
MA /I: B1=0; BI=-105; BD=-105;
MA /M: SY='M'; M=-5,-24,-21,-28,-20,0,-25,-18,18,-18,15,22,-23,-23,-14,-17,-17,-6,16,-11,-2,-17;
MA /M: SY='Q'; M=-8,4,-23,5,6,-23,-16,10,-21,1,-21,-10,4,-13,11,2,6,2,-18,-27,-5,7;
MA /M: SY='I'; M=-7,-30,-21,-34,-27,3,-34,-27,34,-27,27,17,-26,-26,-23,-24,-20,-7,29,-23,-3,-27;
MA /M: SY='T'; M=-9,-3,-18,-12,-10,4,-20,-12,-8,-8,-3,-5,3,-19,-10,-6,-1,12,-7,-21,-3,-9;
MA /M: SY='V'; M=-5,-30,-15,-31,-26,7,-31,-26,26,-25,25,14,-29,-29,-26,-21,-18,-5,32,-24,-4,-26;
MA /M: SY='K'; M=-11,-3,-28,-4,4,-25,-19,0,-25,31,-24,-6,-1,-9,7,25,-7,-7,-18,-22,-8,5;
MA /M: SY='T'; M=-1,-4,-16,-12,-12,-10,-18,-9,0,-10,-6,0,1,-17,-9,-10,4,11,3,-29,-10,-11;
MA /I: MD=-17;
MA /M: SY='L'; M=-9,-16,-24,-17,-8,-6,-23,-14,2,-10,7,5,-13,-11,-6,-7,-12,-6,-2,-23,-7,-8;
MA /I: MD=-17;
MA /M: SY='Q'; M=-7,7,-23,6,3,-26,-3,-3,-23,4,-20,-10,7,-13,10,5,2,-2,-20,-25,-14,6; D=-3;
MA /I: MD=-17;
MA /M: SY='G'; M=-1,1,-26,2,3,-30,14,-1,-28,-3,-23,-12,2,-13,9,-6,1,-11,-24,-22,-17,6; D=-3;
MA /I: I=-4; MI=0; MD=-17; IM=0; DM=-17;
MA /M: SY='Q'; M=-12,7,-25,8,10,-22,-14,7,-25,9,-21,-11,7,-13,12,12,-1,-5,-22,-25,-9,10; D=-3;
MA /I: DM=-17;
MA /M: SY='T'; M=-3,-1,-19,-1,-2,-18,-13,-13,-12,-5,-13,-10,-2,-13,-3,-8,9,11,-6,-30,-14,-1;
MA /I: DM=-17;
MA /M: SY='I'; M=-6,-15,-21,-22,-18,5,-23,-11,7,-18,1,1,-7,-21,-15,-14,-6,-3,5,-16,0,-17;
MA /M: SY='E'; M=-6,-5,-21,-5,10,-14,-21,-12,-11,-2,-11,-9,-5,-7,2,-6,3,8,-8,-26,-11,6;
MA /M: SY='I'; M=-8,-24,-20,-28,-22,12,-29,-15,17,-21,13,9,-21,-25,-19,-18,-15,-4,17,-16,7,-21;
MA /M: SY='E'; M=-10,9,-24,11,15,-15,-17,-2,-21,-3,-17,-15,5,-11,3,-4,4,2,-18,-28,-10,9;
MA /M: SY='V'; M=-5,-26,-19,-30,-25,12,-20,-23,15,-23,13,11,-22,-25,-24,-20,-14,-6,18,-18,-1,-24;
MA /M: SY='E'; M=-5,1,-25,3,9,-22,-9,-9,-26,9,-23,-15,1,-7,4,6,3,-1,-19,-26,-15,6;
MA /M: SY='P'; M=-5,-13,-26,-11,-4,-16,-15,-16,-5,-13,-6,-6,-11,8,-10,-13,-6,-6,-7,-28,-17,-9;
MA /M: SY='S'; M=-1,2,-21,3,10,-26,-10,-8,-23,6,-24,-14,3,-9,10,1,13,8,-17,-29,-15,10;
MA /M: SY='E'; M=-8,8,-27,12,13,-24,-14,-3,-21,3,-18,-7,2,-7,8,-2,-2,-7,-20,-22,-14,10;
MA /M: SY='T'; M=0,-2,-13,-9,-8,-13,-18,-17,-10,-10,-12,-10,0,-7,-7,-10,17,35,-2,-31,-12,-8;

TABLE 1-continued

PROSITE PROFILE PS50053

MA /M: SY='V'; M=−2,−25,−14,−29,−27,−1,−30,−27,28,−20,9,11,−24,−25,−24,−20,−8,5,38,−28,−8,−26;
MA /M: SY='Q'; M=0,−6,−22,−6,0,−15,−11,−5,−16,−3,−12,−8,−4,−10,3,−6,1,−4,−14,−23,−8,1;
MA /M: SY='E'; M=−8,−1,−24,1,12,−20,−20,4,−12,−5,−7,−5,−2,−14,8,−6,−3,−6,−12,−28,−9,9;
MA /M: SY='L'; M=−10,−25,−22,−28,−19,7,−30,−20,16,−19,27,13,−22,−25,−17,−12,−22,−7,10,−19,0,−19;
MA /M: SY='K'; M=−8,−2,−29,−3,7,−28,−20,−11,−25,42,−26,−9,−1,−11,8,27,−10,−10,−17,−20,−10,7;
MA /M: SY='E'; M=−1,−1,−23,0,11,−22,−17,−6,−15,2,−9,−7,−3,−13,11,0,−3,−5,−14,−25,−13,10;
MA /M: SY='H'; M=−10,−9,−26,−11,−2,−19,−22,13,−11,8,−8,6,−6,−17,10,6,−11,−11,−11,−22,−2,3;
MA /I: MD=−25;
MA /M: SY='I'; M=−7,−22,−24,−26,−18,−4,−27,−23,25,−22,14,10,−17,−22,−17,−21,−15,−8,19,−24,−7,−20;
MA /I: MD=−25;
MA /M: SY='E'; M=8,−1,−20,−3,12,−22,−12,−3,−17,0,−16,−11,0,−9,8,−1,6,−1,−14,−25,−15,9; D=−5;
MA /I: I=−6; MI=0; IM=0; DM=−25;
MA /M: SY='E'; M=−7,6,−27,11,13,−29,−1,−3,−28,4,−24,−15,3,−11,12,1,2,−8,−25,−25,−14,12;
MA /I: DM=−25;
MA /M: SY='R'; M=−5,−7,−24,−7,4,−19,−18,−10,−14,8,−13,−8,−4,−10,1,13,−3,−5,−10,−25,−13,1;
MA /M: SY='E'; M=−10,−2,−26,−2,8,−18,−19,−7,−6,−4,−7,−2,−4,−13,6,−7,−6,−5,−9,−23,−7,6;
MA /M: SY='G'; M=5,−4,−24,−7,−9,−26,33,−15,−30,−9,−26,−17,3,−16,−10,−10,7,−7,−22,−24,−24,−10;
MA /M: SY='V'; M=−7,−23,−15,−27,−22,−1,−28,−22,17,−15,3,9,−18,−19,−18,−14,−10,−4,19,−24,−6,−21;
MA /M: SY='P'; M=−9,−9,−33,−2,7,−27,−19,1,−21,−5,−23,−14,−9,40,2,−9,−7,−10,−26,−29,−18,1;
MA /M: SY='P'; M=0,−13,−23,−12,−4,−17,−18,−15,−2,−10,−9,0,−13,9,−6,−14,−2,−2,−1,−28,−16,−6;
MA /M: SY='D'; M=−2,13,−22,15,9,−21,2,−7,−26,−6,−23,−20,11,−12,−3,−10,8,−4,−21,−30,−18,3;
MA /M: SY='Q'; M=−9,3,−26,4,9,−19,−10,−4,−23,−4,−20,−11,3,−13,13,3,1,−6,−21,−24,−11,11;
MA /M: SY='Q'; M=−11,−9,−28,−11,6,−21,−24,0,−5,−2,−6,5,−7,−15,34,0,−7,−10,−16,−18,−5,20;
MA /M: SY='R'; M=−12,−11,−28,−12,−3,−19,−20,−9,−22,25,−19,−9,−7,−18,3,38,−11,−10,−13,−8,−8,−2;
MA /M: SY='L'; M=−10,−30,−19,−31,−23,19,−30,−21,18,−29,40,16,−29,−30,−24,−20,−26,−9,13,−17,3,−23;
MA /M: SY='I'; M=−5,−24,−24,−30,−21,0,−30,−19,25,−23,21,15,−19,−22,−13,−21,−16,−6,14,−18,1,−19;
MA /I: MD=−20;
MA /M: SY='F'; M=−13,−22,−23,−26,−20,34,−26,−2,−1,−16,5,1,−17,−27,−20,−13,−16,−8,−3,5,34,−20;
MA /I: I=−8; MI=−15; IM=−15; DM=−15; MD=−15;
MA /M: SY='E'; M=4,9,−23,13,14,−29,−6,−7,−26,5,−23,−17,4,−9,8,−4,7,−4,−20,−29,−18,11;
MA /I: DM=−20;
MA /M: SY='G'; M=−1,−6,−29,−6,−17,−30,62,−19,−39,−19,−29,−20,1,−19,−19,−19,1,−17,−29,−21,−29,−18;
MA /M: SY='K'; M=−7,−8,−27,−10,0,−21,−21,−9,−14,21,−15,−2,−5,−15,7,20,−8,−8,−10,−21,−9,2;
MA /M: SY='V'; M=−7,−19,−24,−20,−10,−6,−25,−16,2,−10,−1,0,−16,−6,−8,−4,−10,−6,3,−22,−8,−10;
MA /M: SY='L'; M=−10,−30,−21,−32,−22,7,−31,−21,25,−29,42,21,−28,−28,−20,−21,−27,−10,15,−20,0,−22;
MA /M: SY='E'; M=−8,7,−27,9,19,−29,−16,3,−25,13,−21,−11,5,−10,18,9,−1,−8,−23,−27,−13,18;
MA /M: SY='D'; M=−11,40,−27,55,18,−37,−9,−2,−36,−1,−28,−27,16,−10,0,−11,3,−8,−26,−38,−20,9;
MA /I: MD=−20;
MA /M: SY='D'; M=−9,15,−25,16,8,−26,−1,1,−27,1,−24,−15,15,−13,3,−2,5,−4,−23,−32,−17,5;
MA /I: I=−8; MI=−15; IM=−15; DM=−15; MD=−15;
MA /M: SY='Q'; M=−5,−6,−23,−9,2,−19,−20,−3,−10,6,−7,1,−5,−16,11,4,−6,−4,−10,−23,−8,6;
MA /I: DM=−20;
MA /M: SY='T'; M=−1,−7,−11,−12,−9,−11,−19,−19,−12,−10,−13,−11,−5,2,−11,−12,11,26,−6,−29,−13,−10;
MA /M: SY='L'; M=−7,−27,−21,−26,−18,0,−27,−20,15,−23,26,13,−26,−11,−18,−19,−20,−7,11,−24,−7,−19;
MA /M: SY='S'; M=4,−1,−21,−1,−3,−26,5,−10,−25,0,−23,−15,2,−12,3,−1,10,0,−18,−27,−19,2;
MA /M: SY='D'; M=−6,16,−26,24,24,−24,−14,−2,−27,0,−21,−19,5,−8,7,−7,3,−6,−23,−28,−13,16;
MA /M: SY='Y'; M=−9,−21,6,−24,−20,7,−27,−5,−2,−19,8,0,−21,−30,−14,−17,−17,−9,−4,−7,23,−19;
MA /M: SY='G'; M=−7,8,−28,6,−7,−28,30,0,−34,−6,−29,−18,15,−18,−8,−7,0,−14,−29,−27,−20,−8;
MA /M: SY='I'; M=−9,−28,−22,−34,−25,7,−31,−21,30,−25,26,25,−24,−25,−19,−21,−21,−8,22,−20,0,−23;
MA /M: SY='E'; M=−2,5,−24,6,15,−27,−9,−6,−23,5,−21,−13,3,−10,11,−1,4,−1,−19,−27,−16,13;
MA /M: SY='D'; M=−7,16,−28,25,17,−31,−12,−7,−29,1,−27,−22,6,12,1,−8,3,−6,−25,−34,−21,8;
MA /M: SY='G'; M=−4,−2,−27,−2,1,−25,15,−10,−26,−4,−18,−12,1,−16,0,−4,−2,−11,−22,−24,−19,0;
MA /M: SY='B'; M=−2,12,−5,9,−1,−23,−11,−4,−21,−8,−21,−15,10,−15,−2,−10,11,8,−15,−35,−16,−2;
MA /M: SY='T'; M=−2,−8,−17,−13,−6,−7,−20,−15,−7,−6,−9,−6,−5,−14,−4,−5,7,16,−1,−25,−8,−5;
MA /M: SY='V'; M=−5,−28,−18,−32,−27,1,−33,−28,32,−24,19,14,−25,−26,−24,−23,−15,−2,34,−25,−5,−27;
MA /M: SY='H'; M=−12,−8,−25,−8,0,−8,−24,18,−4,−11,−3,4,−7,−18,−3,−10,−10,−9,−4,−23,4,−8;
MA /M: SY='L'; M=−1,−24,−17,−27,−19,4,−24,−19,14,−19,23,15,−23,−25,−18,−16,−16,−4,15,−21,−4,−18;
MA /M: SY='M'; M=−1,−15,−18,−20,−17,−7,−21,−1,10,−13,1,13,−11,−22,−9,−13,−8,−6,13,−24,−2,−14;
MA /M: SY='L'; M=−7,−18,−20,−18,−16,−7,−14,−18,5,−14,10,7,−18,−25,−14,−10,−14,−8,10,−24,−10,−16;
MA /M: SY='R'; M=−11,−1,−26,−1,7,−22,−19,−1,−22,16,−20,−10,1,−13,8,23,0,0,−1,6,−25,−10,5;
MA /M: SY='Q'; M=−9,−6,−26,−7,6,−21,−16,−4,−12,7,−5,5,−6,−15,14,3,−10,−10,−15,−22,−9,10;
MA /M: SY='R'; M=−9,−10,−15,−12,−7,−18,−20,−13,−16,1,−14,−10,−5,1,−5,11,−4,0,−13,−28,−15,−8;
MA /M: SY='G'; M=−2,−1,−26,−2,−9,−27,33,−14,−33,−4,−29,−18,5,−16,−9,−8,6,−8,−24,−25,−23,−9;
MA /M: SY='G'; M=3,−9,−28,−8,−8,−28,39,−18,−32,−15,−28,−19,−3,−1,−13,−18,2,−13,−26,−24,−28,−12;
MA /I: E1=0; IE=−105; DE=−105;
NR /RELEASE=38,80000;
NR /TOTAL=68(65); /POSITIVE=64(61); /UNKNOWN=4(4); /FALSE_POS=0(0);
NR /FALSE_NEG=0; /PARTIAL=0;
CC /TAXO-RANGE=??E?V; /MAX-REPEAT=12;
CC /FT_KEY=DOMAIN; /FT_DESC=UBIQUITIN-LIKE;
DR Q10235, AL11_SCHPO, T; Q99933, BAG1_HUMAN, T; Q60739, BAG1_MOUSE, T;
DR P46379, BAT3_HUMAN, T; Q99426, CKAP_HUMAN, T; P48510, DSK2_YEAST, T;
DR Q15843, NED8_HUMAN, T; P29595, NED8_MOUSE, T; P54725, R23A_HUMAN, T;
DR P54726, R23A_MOUSE, T; P54727, R23B_HUMAN, T; P54728, R23B_MOUSE, T;
DR P32628, RA23_YEAST, T; Q15459, S114_HUMAN, T; P55854, SM31_HUMAN, T;
DR P55855, SM32_HUMAN, T; Q93068, SM33_HUMAN, T; P55852, SMT3_ARATH, T;
DR P55853, SMT3_CAEEL, T; P55857, SMT3_ORYSA, T; O13351, SMT3_SCHPO, T;

TABLE 1-continued

PROSITE PROFILE PS50053

DR Q12306, SMT3_YEAST, T; P54578, TGT_HUMAN, T; P40826, TGT_RABIT, T;
DR Q07371, UBIL_CAEBR, T; Q07372, UBIL_CAEEL, T; P11441, UBIL_HUMAN, T;
DR P21126, UBIL_MOUSE, T; P16709, UBIL_NPVAC, T; Q05120, UBIL_NPVOP, T;
DR Q60435, UBIM_CRIGR, T; P35544, UBIM_HUMAN, T; P35545, UBIM_MOUSE, T;
DR P55812, UBIM_PIG , T; Q05474, UBIM_RAT , T; P49634, UBIQ_ACACA, T;
DR P42739, UBIQ_ACECL, T; P42740, UBIQ_AGLNE, T; P14792, UBIQ_CAEEL, T;
DR P14624, UBIQ_CHLRE, T; P19848, UBIQ_COPCO, T; P08618, UBIQ_DICDI, T;
DR P46574, UBIQ_EIMBO, T; P23324, UBIQ_EUPEU, T; P02248, UBIQ_HUMAN, T;
DR Q05550, UBIQ_LEIMA, T; P49635, UBIQ_LEITA, T; P13117, UBIQ_NEUCR, T;
DR P22589, UBIQ_PHYIN, T; P03993, UBIQ_SOYBN, T; P23398, UBIQ_STRPU, T;
DR P20685, UBIQ_TETPY, T; P15174, UBIQ_TRYBB, T; P08565, UBIQ_TRYCR, T;
DR P04838, UBIQ_YEAST, T; Q92353, UBPC_SCHPO, T; Q10169, YAUG_SCHPO, T;
DR Q20728, YXHK_CAEEL, T; O02741, UCRP_BOVIN, T; P05161, UCRP_HUMAN, T;
DR Q64339, UCRP_MOUSE, T;
DR Q15011, YO25_HUMAN, ?; P34256, YKA4_CAEEL, ?; Q03714, YMC9_YEAST, ?;
DR P34675, YO25_CAEEL, ?;
3D 1NDD; 1UBA; 1A5R; 1UBQ; 1UBI; 1AAR; 1TBE;
DO PDOC00271;
//

TABLE 2

PROSITE DOMAIN PS00299

| Residue | Amino acid(s) |
| --- | --- |
| 1 | Lys |
| 2 | Xaa |
| 3 | Xaa |
| 4 | Leu/Ile/Val/Met |
| 5 | Xaa |
| 6 | Asp/Glu/Ser/Ala/Lys |
| 7 | Xaa |
| 8 | Xaa |
| 9 | Xaa |
| 10 | Leu/Ile/Val/Met |
| 11 | Pro/Ala |
| 12 | Xaa |
| 13 | Xaa |
| 14 | Xaa |
| 15 | Gln |
| 16 | Xaa |
| 17 | Leu/Ile/Val/Met |
| 18 | Leu/Ile/Val/Met/Cys |
| 19 | Leu/Ile/Val/Met/Phe/Tyr |
| 20 | Xaa |
| 21 | Gly |
| 22 | Xaa |
| 23 | Xaa |
| 24 | Xaa |
| 25 | Xaa |
| 26 | Asp/Glu |

REFERENCES (THE CONTENTS OF WHICH ARE HEREBY INCORPORATED IN FULL)

1—Demidov et al. (2000) *Curr Issues Mol. Biol.* 2(1):31-35.
2—Bukanov et al. (1998) *Proc. Natl. Acad. Sci. USA* 95(10) 5516-5520.
3—U.S. Pat. No. 6,265,166.
4—Wong et al. (2000) *Biotechniques* 28(4):776-783.
5—International patent application PCT/GB01/02564.
6—UK patent application 0014324.8 (GB-A-2363381).
7—Baker et al. (2001) *Biotechniques* 31(1): 142-145.
8—International patent application PCT/GB99/03357 (WO00/21973).
9—International patent application PCT/US99/30751 (WO00/37686).
10—Hofmann et al. (1999) *Nucleic Acids Research* 27(1): 215-219.
11—Bucher & Bairoch (1994) *Proc. Int. Conf. Intell. Syst. Mol. Biol.* 2:5361 [ISMB-94; *Proceedings 2nd International Conference on Intelligent Systems for Molecular Biology.* (eds. Altman et al.), AAAIPress, Menlo Park].
12—Silverstein et al. (2001) *Nucleic Acids Research* 29(1): 49-51.
13—Shoop et al. (2001) *Bioinformatics* 17(3):262-271.
14—Silverstein et al. (2001) *Bioinformatics* 17(3):249-261.
15—Apweiler et al. (2000) *Bioinformatics* 16(12):1145-1150.
16—Apweiler et al. (2000) *Nucleic Acids Research* 29(1): 3740.
17—Lo Conte et al. (2000) *Nucleic Acids Research* 28(1): 257-259.
18—Armstrong & Quigley (1999) *Dev Conmp Immunol* 23(4-5):375-390.
19—Feige et al. (1996) *Horm Res* 45(3-5):227-232.

---

The invention claimed is:

1. A method for increasing the yield of a nucleic acid duplex during purification process, comprising the step of contacting a nucleic acid duplex with a composition which comprises divalent cations and a purified ubiquitin-like protein, wherein:
 a) the ubiquitin-like protein comprises the following amino acid sequence (SEQ ID NO: 1): KXXX$^1$XX$^2$XXXX$^3$X$^4$XXXQXX$^5$X$^6$X$^7$XGXXXXX$^8$ wherein
 X is any amino acid,
 X$^1$, X$^3$, and X$^5$ are each independently selected from L, I, V or M,
 X$^2$ is D, E, S, A or K,
 X$^4$ is P or A,
 X$^6$ is L, I, V, M or C,
 X$^7$ is L, I, V, M, F or Y, and
 X$^8$ is D or E;
 and
 b) the ubiquitin-like protein is selected from the group consisting of a fusion protein, a tandem repeat protein, a precursor, a mature protein, glycosylated, unglycosylated, methylated, labeled, and with or without N-terminal methionine provided that duplex stabilization activity is retained.

2. The method according to claim 1, wherein the composition is in the form of an aqueous solution.

3. The method according to claim 1, wherein the ubiquitin-like protein is a NEDD8, a ubiquitin or a RAD23 protein.

4. The method according to claim 1, wherein the ubiquitin-like protein is present at a concentration of between 0.1 and 20 mg/ml.

5. The method according to claim 1, wherein the ubiquitin-like protein is present in the form of an oligomer.

6. The method according to claim 1, wherein the composition has a pH between 3 and 11.

7. The method according to claim 1, wherein the divalent cations are at a concentration between 0.1 mM and 10 mM.

8. The method according to claim 1, wherein the nucleic acid duplex is double-stranded DNA.

9. The method of claim 1, wherein: (i) the ubiquitin-like protein comprises at least 50% by weight of the total protein in the composition or (ii) the composition further comprises monovalent cations at a concentration between 0.1 mM and 10 mM.

10. The method according to claim 1, wherein the divalent cation is Mg$^{2+}$.

11. The method of claim 1, wherein: (i) the ubiquitin-like protein comprises at least 50% by weight of the total protein in the composition and (ii) the composition further comprises monovalent cations at a concentration between 0.1 mM and 10 mM.

* * * * *